US011291696B2

(12) United States Patent
Morris et al.

(10) Patent No.: US 11,291,696 B2
(45) Date of Patent: Apr. 5, 2022

(54) PAIRING PROBIOTICS AND PREBIOTICS, METHODS FOR GROWTH AND USE, SEPARATELY AND IN COMBINATION

(71) Applicants: Shayne Morris, Ogden, UT (US); Michael Benson, Newton, UT (US)

(72) Inventors: Shayne Morris, Ogden, UT (US); Michael Benson, Newton, UT (US)

(*) Notice: Subject to any disclaimer, the term of this patent is extended or adjusted under 35 U.S.C. 154(b) by 111 days.

(21) Appl. No.: 16/886,399

(22) Filed: May 28, 2020

(65) Prior Publication Data
US 2020/0316142 A1 Oct. 8, 2020

Related U.S. Application Data

(63) Continuation-in-part of application No. 16/380,226, filed on Apr. 10, 2019, now Pat. No. 11,168,299.

(60) Provisional application No. 62/655,935, filed on Apr. 11, 2018, provisional application No. 62/854,490, filed on May 30, 2019.

(51) Int. Cl.
A61K 35/742 (2015.01)
A61K 35/744 (2015.01)
A61K 9/19 (2006.01)
C12N 1/20 (2006.01)

(52) U.S. Cl.
CPC ............. A61K 35/742 (2013.01); A61K 9/19 (2013.01); A61K 35/744 (2013.01); C12N 1/20 (2013.01)

(58) Field of Classification Search
CPC ...... A61K 35/742; A61K 9/19; A61K 35/744; C12N 1/20
USPC ..................................................... 424/93.41
See application file for complete search history.

(56) References Cited

U.S. PATENT DOCUMENTS

| | | | |
|---|---|---|---|
| 6,468,525 | B1 | 10/2002 | Watson et al. |
| 7,214,370 | B2 | 5/2007 | Naidu |
| 8,309,073 | B2 | 11/2012 | Mayra-Makinen et al. |
| 8,318,152 | B2 | 11/2012 | Lin |
| 8,460,648 | B2 | 6/2013 | Borody |
| 8,815,538 | B2 | 8/2014 | Lanzalaco et al. |
| 9,370,476 | B2 | 6/2016 | Kleinberg et al. |
| 2003/0180260 | A1 | 9/2003 | Clancy et al. |
| 2008/0267933 | A1 | 10/2008 | Ohlson et al. |
| 2009/0110664 | A1 | 4/2009 | Moore |
| 2010/0316769 | A1 | 12/2010 | Czarnecki-Maulden et al. |
| 2012/0087895 | A1 | 4/2012 | Mazmanian et al. |
| 2013/0273155 | A1 | 10/2013 | Yonak et al. |
| 2013/0288261 | A1 | 10/2013 | Walter et al. |

FOREIGN PATENT DOCUMENTS

| | | |
|---|---|---|
| WO | WO2011096809 | 8/2011 |
| WO | WO2014075745 | 5/2014 |
| WO | WO2014127351 | 8/2014 |

OTHER PUBLICATIONS

Salava and Lauerma Clinical and Translational Allergy 2014, 4:33 http://www.ctajournal.com/content/4/1/33.
The New England Journal of Medicine, Endogenous Antimicrobial Peptides and Skin Infections in Atopic Dermatitis, Peck Y. Ong, MD, Takaaki Ohtake, MD, PhD, Corinne Brandt, S.S., Ian Strickland, PhD, Mark Boguniwicz, MD, Tomas Ganz, MD, PhD, Richard L. Gallo, MD, PhD, and Donald Y.M. Leung, MD, PhD, vol. 347, No. 15, Oct. 10, 2002.
J Invest Dermatol, Staphylococcus aureus exploits epidermal barrier defects in atopic dermatitis to trigger cytokine expression, Teruaki Nakatsuji, Tiffany H. Chen, Aimee M. Two, Kimberly A. Chun, Saisindhu Narala, Raif S. Geha, Tissa R. Hata, and Richard L. Gallo, Nov. 2016, 136(11): 2192-2200.
Current Pharmaceutical Biotechnology, M.C.F Bastos, H. Ceotto, M.L.V. Coelho and J.S. Nascimento, Staphylococcal Antimicrobial Peptides: Relevant Properties and Potential Biotechnological Applications, 2009, vol. 10, pp. 38-61.
Pediatr Res., Lactobacillus rhamnosus GG and its SpaC adhesin modulate inflammatory responsiveness and TLR-related gene expression in the fetal human gut, Kriston Ganguli, Maria Carmen Collado, Jaana Rautava, Lei Lu, Reetta Satokari, Ingemar von Ossowski, Justus Reunanen, Willem M. de Vos, Airi Paiva, Erika Isolauri, Seppo Salminen, W. Allan Walker, and Samuli Rautava, Apr. 2015; 77(4): pp. 528-535.
Clin Exp Allergy, No effects of probiotics on atopic dermatitis in infancy; a randomized placebo-controlled trial, Brouwer ML, Wolt-Plompen SA, Dubois AE, van der Heide S, Jansen DF, Joijer MA, Kauffman HF, Duiverman EJ, Jul. 2006 36(7); pp. 899-906.
European Journal of Allergy and Clinical Immunology, Randomized, placebo-controlled trial of Lactobacillus rhamnosus GG as treatment of atopic dermatitis in infancy, c. Gruber, M. Wendt, C. Sulser, S. Lau, M. Kulig, U. Wahn, T. Werfel, B. Niggermann, Oct. 4, 2007.
Br J Dermatol, Prospective, randomized controlled trial on Lactobacillus rhamnosus in infants with moderate to severe topic dermatitis, Folster-Holst R, Muller F, Schnopp N, Abeck D, Kreiselmaier I, Lenz T, von Ruden U, Schrezenmeir J, Christophers E, Weichenthal M, Dec. 2006. 155(6).
BMC Genomics, Antagonism between Staphylococcus epidermidis and Propionibacterium acnes and its genomic basis, Gitte J.M. Christensen, Christian F.P. Scholz, Jan Enghild, Holger Rohde, Mogens Kilian, Andrea Thumer, Elzieta Brzuszkiewicz, Hans B. Lomholt and Holger Bruggemann, Feb. 2016 17:152.
Appl Microbiol Biotechnol, Staphylococcus epidermidis in the human skin microbiome mediates fermentation to inhibit growth of Propionibacterium acnes: Implications of probiotics in acne vulgaris, Yanhan Wang, Sherwin Kuo, Muya Shu, Jinghua Yu, Stephen Huang, Ashley Dai, Aimee Two, Richard L. Gallo, and Chung-Ming Huang, Jan. 2014; 98(1).

(Continued)

Primary Examiner — Jennifer M. H. Tichy
(74) Attorney, Agent, or Firm — Pate Baird, PLLC

(57) ABSTRACT

A method for growing probiotic organisms wherein the growth media includes prebiotics especially selected and prepared to be paired with the probiotic organisms being grown. The prebiotic formula is optimized to grow the desired probiotic organisms, as well as important byproducts of the growth process. Specialized freeze-drying buffers may also be paired with certain probiotic organisms for the freeze-drying process. Specific products may utilize selected probiotic organisms grown and supported with paired prebiotic formulas to promote and maintain physiological health in a subject.

19 Claims, 2 Drawing Sheets

(56) References Cited

OTHER PUBLICATIONS

Eur. J. Immunol., Lactobacillus casei reduces $CD8^+$ T cell-mediated skin inflammation, Ludivine Chapat, Karine Chemin, Bertrand Dubois, Raphaelle Bourdet-Sicard, and Dominique Kaiserlian, 2004, v. 34, pp. 2520-2528.
Semin Cutan Med Surg., Antimicrobial Peptides, Skin Infections and Atopic Dermatitis, Tissa R. Hata, MD and Richard L. Gallo, MD, Jun. 2008; 27(2); pp. 144-150.
International Journal of Probiotics and Prebiotics, Probiotics to young children with atopic dermatitis: A randomized placebo-controlled trial, R. Gobel, N Larsen, C Molgaard, M Jakobsen, and KF Michaelsen, Apr. 2010 vol. 5, No. 2, pp. 53-60.
Annals of Nutrition & Metabolism, Probiotics in the Treatment and Prevention of Atopic Dermatitis, R. Folster-Holst, Sep. 8, 2010; 57(suppl 1):16-19.
British Journal of Dermatology, The role of the skin microbiome in atopic dermatitis: a systematic review, R.D. Bjerre, J. Bandier, L. Skov, L. Engstrand, and J.D. Johansen, 2017 vol. 177, pp. 1272-1278.

| Probiotic Organism | Acetic Acid mg/ml | D(-) Lactic Acid mg/ml | Propionic Acid mg/ml | Valeric Acid mg/ml | Butyric Acid mg/ml | Hexanoic Acid mg/ml |
|---|---|---|---|---|---|---|
| M. vaccae | 0.00 | 1.02 | 0.00 | 0.01 | 0.00 | 0.06 |
| C. symbiosum | 9.46 | 12.50 | 0.00 | 0.02 | 3.39 | 0.08 |
| E. limosum | 17.71 | 0.00 | 0.00 | 0.63 | 7.05 | 0.80 |
| B. uniformis | 6.93 | 14.91 | 1.09 | 0.83 | 0.00 | 0.26 |
| B. thetaiotaomicron | 5.91 | 14.73 | 0.00 | 0.32 | 7.59 | 0.05 |
| P. acidilactici | 57.80 | 126.17 | 0.14 | 0.00 | 16.68 | 0.05 |
| B. fragilis | 7.74 | 16.40 | 1.43 | 0.42 | 10.05 | 0.15 |

FIGURE 1

PAIRING PROBIOTICS AND PREBIOTICS, METHODS FOR GROWTH AND USE, SEPARATELY AND IN COMBINATION

RELATED APPLICATIONS

This application is a continuation-in-part of U.S. patent application Ser. No. 16/380,226, filed Apr. 10, 2019; which claims the benefit of U.S. Provisional Patent Application Ser. No. 62/655,935, filed on Apr. 11, 2018; and this application claims the benefit of U.S. Provisional Patent Application Ser. No. 62/854,490, filed on May 30, 2019; all of which are hereby incorporated by reference in their entireties.

BACKGROUND

The Field of the Invention

This invention relates to methods for producing and using probiotics, and more particularly to the pairing of particular probiotics and prebiotics to optimize growth and usefulness of the probiotics, both in vivo and in vitro.

Background

Numerous products contain probiotics for a variety of purposes. These purposes may include regulating digestion, improving and maintaining health in general, or improving specific physiological systems, as well as other purposes. The probiotic *Lactobacillus acidophilus* is an example of the use of probiotics as a nutritional supplement, or as a component in foods such as yogurts.

Generally, probiotics may be grown or cultured using a broth and/or an agar spread plate. There are various formulations for such a broth and various media used for such agar spread plates. These formulations are relatively standardized for both broths and agar spread plates.

Methods for growing and culturing common probiotics, like *Lactobacillus acidophilus*, are generally established. For example, an original strain of the desired probiotic may be obtained and used an inoculation material. The inoculation material may be grown in a fermenter (i.e., a liquid broth) and/or on a surface (i.e., an agar plate). This growth generally happens under pre-defined and monitored conditions. The grown probiotic may then be harvested. After being harvested, the probiotic may be blended with other probiotics. The single probiotic or blend of probiotics may be preserved in some manner for transportation and/or storage.

While there are various, useful probiotics that are found in nature, not all probiotics are available for commercial use. What is needed is an improved method or methods for culturing and harvesting more types of probiotics. Moreover, to get the full benefit of certain probiotics, those probiotics should be cultured or grown with the most appropriate prebiotics, or prebiotics specifically matched to optimize the growth of the desired probiotics. What is needed is an improved method or methods for producing or culturing various, useful probiotics to fully realize the potential and benefits of those probiotics.

BRIEF SUMMARY OF THE INVENTION

In accordance with the foregoing, certain embodiments of a probiotic product and/or method for production in accordance with the invention may provide probiotics that can be used for a variety of purposes, including without limitation, nutritional supplements, topical applications, and related uses and products.

There are a number of probiotic organisms that may be considered useful and helpful to promote or maintain health in humans and animals. Such probiotics may include *Bacteroides thetaiotaomicron, Bacteroides fragilis, Bacteroides ovatus, Bacteroides uniformis, Faecalibacterium prausnitzii, Akkermansia muciniphila, Eubacterium rectale, Collinsella aerofaciens, Desulfovibrio piger, Clostridium symbiosum, Mycobacterium vaccae, Eubacterium limosum, Butyricicoccus pullicaecorum, Roseomonas mucosa, Lactobacillus farciminis, Staphylococcus epidermis, Staphylococcus xylosus, Pediococcus acidilactici, Roseburia hominis,* and *Anaerostipes caccae*. These probiotics, and methods for growing them, are primarily described herein, but the methods and formulations described herein may be applicable to other probiotic organisms.

A method for growing probiotic organisms, or growing unique probiotic fermentations, may comprise a number steps. The method may include selecting a probiotic organism to grow. The method may include selecting a growth broth for growing the probiotic organism, wherein the growth broth includes a prebiotic formulation that is optimized for the selected probiotic organism. The method may include inoculating the growth broth with the probiotic organism. The method may include growing the probiotic organism in the growth broth and harvesting the probiotic organism from the growth broth. The method may include selecting an agar spread plate for growing the probiotic organism, wherein the agar spread plate media includes a prebiotic formula that is optimized for growing the probiotic organism. The method may include inoculating the agar spread plate with the probiotic organism harvested from the growth broth. The method may include growing the probiotic organism on the agar spread plate and harvesting the probiotic organism from the agar spread plate.

A method may further include freeze-drying the harvested probiotic organism with a lyophilization reagent. The lyophilization reagent may be comprised of one or more of the following: glucosamine, glutamine, sucrose, mannitol, trehalose, glycerol, inositol, raffinose, inulin, powdered skim milk, activated charcoal, soluble starch, collagen powder, chondroitin sulfate, glucosamine sulfate, guar, acacia, silica, and fructooligosaccharide P95.

A method as described herein may be used for growing any of the probiotic organisms included, as well as other probiotic organisms. A method may include the use of a specific formulation of prebiotics that are optimized for, or preferentially paired with, specific probiotic organisms. This pairing of certain prebiotics with certain probiotics helps promote better and faster growth of the desired probiotic. The use of certain, important prebiotics can promote the growth of a probiotic organism and specific byproducts of importance. Thus, a prebiotic, or prebiotic formulation, may be selected to be paired with a probiotic organism both for growing the probiotic organism and a desired byproduct, or group of byproducts, that may be helpful or important for a given purpose.

A method as described herein may be used for growing probiotic organisms that are utilized in products designed to promote the health and maintenance of a specific physiological system or function. For example and not by way of limitation, a product may include specific probiotic organisms that promote the health and maintenance of the immune system. Such a product may include a specific prebiotic formulation to support the specific probiotic organisms in vivo. Similarly, a product may include specific probiotic organisms that promote and maintain neurological functions. Such a product may include a specific prebiotic formulation to support the specific probiotic organisms in vivo.

BRIEF DESCRIPTION OF THE DRAWINGS

The foregoing features of the present invention will become more fully apparent from the following description and appended claims, taken in conjunction with the accompanying drawings and experimental data. Understanding that these drawings and date depict only typical embodiments of the invention and are, therefore, not to be considered limiting of its scope, the invention will be described with additional specificity and detail through use of the accompanying drawings and data in which:

FIG. 1 illustrates a table providing results of measuring the amount of certain short chain fatty acids produced from certain probiotic organisms, where the values for short chain fatty acids are in milligrams per milliliter measured from culture supernatant.

DETAILED DESCRIPTION OF THE PREFERRED EMBODIMENTS

Figure 2:
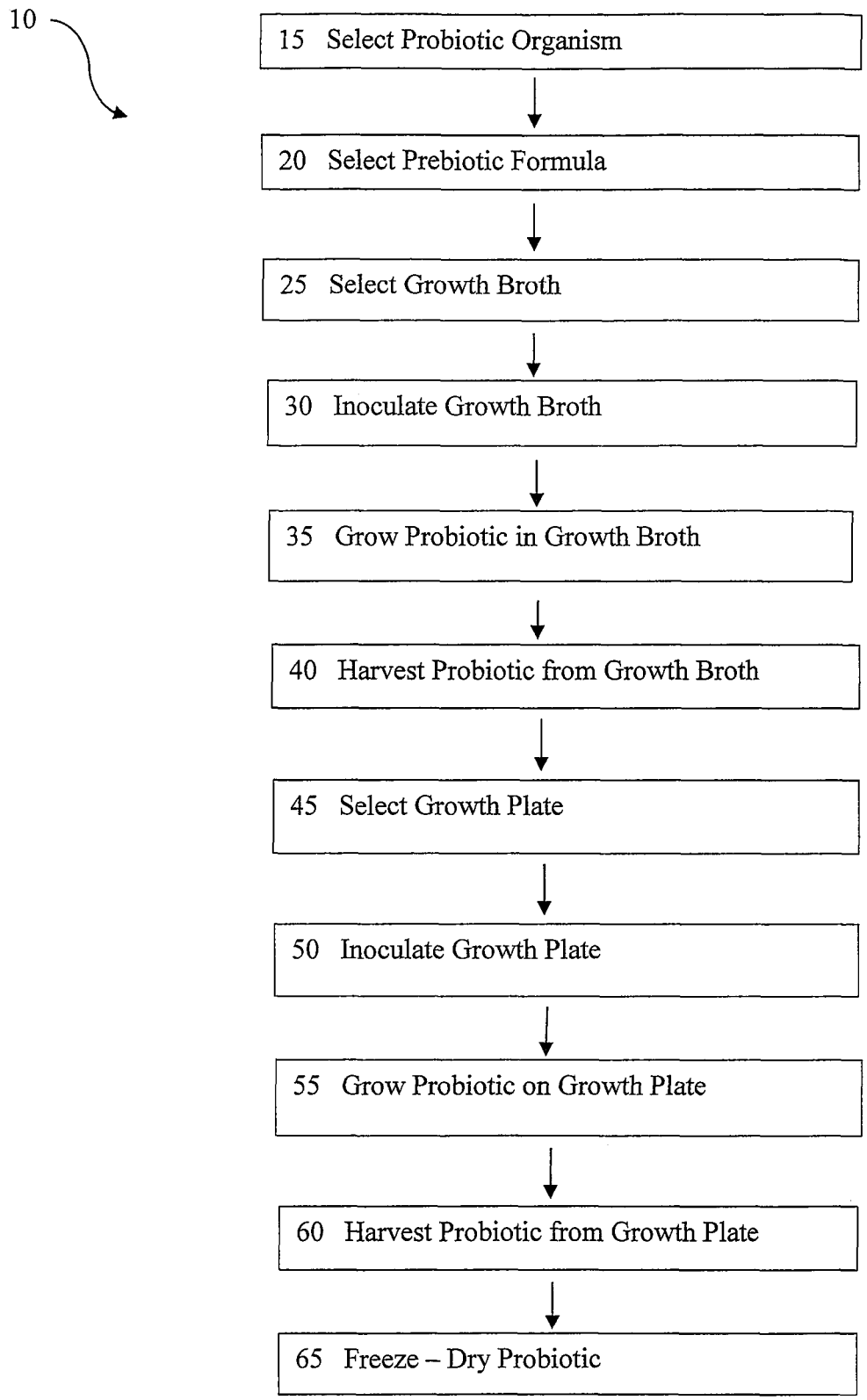
FIG. 2 is a schematic diagram of an embodiment of a method for growing probiotic organisms.

It will be readily understood that the components of the present invention, as generally described herein, could be arranged and designed in a wide variety of different configurations or formulations. Thus, the following more detailed description of the embodiments of the system, product and method of the present invention, is not intended to limit the scope of the invention, as claimed, but is merely representative of various embodiments of the invention.

In one embodiment, a method for growing or culturing numerous probiotic organisms may include the following steps: selecting a probiotic organism, or a group of probiotic organisms, to grow; selecting a growth broth, which may include a prebiotic formulation specially designed to help grow the probiotic organism selected; growing the probiotic organism in the growth broth; harvesting the probiotic organism from the growth broth; selecting a growth plate, which may include a prebiotic formulation specially designed to help grow the probiotic organism selected; growing the probiotic organism on the growth plate; and harvesting the probiotic organism from the growth plate.

A probiotic organism, or a group of organisms, grown in this manner can be freeze-dried after harvesting to prepare the organism for transfer and/or storage.

The various steps in the process for growing a probiotic organism may include variations at every level. For example, and not by way of limitation, a growth broth may or may not include a prebiotic formula specially selected for the probiotic organism being grown. A prebiotic formula may be specifically designed for one or more probiotic organisms, thereby allowing for numerous and varied formulations for prebiotic formulas. Also, the conditions for growing certain probiotic organisms can vary.

Generally, a probiotic organism grown in accordance with the disclosed method will be one or more of the following: *Bacteroides thetaiotaomicron, Bacteroides fragilis, Bacteroides ovatus, Bacteroides uniformis, Faecalibacterium prausnitzii, Akkermansia muciniphila, Eubacterium rectale, Collinsella aerofaciens, Desulfovibrio piger, Clostridium symbiosum, Mycobacterium vaccae, Eubacterium limosum, Butyricicoccus pullicaecorum, Roseomonas mucosa, Lactobacillus farciminis, Staphylococcus epidermis, Staphylococcus xylosus, Pediococcus acidilactici, Roseburia hominis,* and *Anaerostipes caccae.*

In one embodiment, a growth broth, or liquid growth medium, may be comprised of approximately 26 grams of tryptic soy broth, approximately 4 grams of inulin, and approximately 0.4 grams of cysteine in approximately 900 milliliters of water. Such a growth broth may be kept and/or used in a sealed one liter bottle. Such a growth broth may be used to grow a probiotic organism, for example and not by way of limitation, *Bacteroides fragilis, Bacteroides ovatus, Bacteroides uniformis, Eubacterium limosum, Clostridium symbiosum, Parabacteroides distasonis,* and *Parabacteroides goldsteinii.*

In one embodiment, a growth broth, or liquid growth medium, may be comprised of approximately 26 grams of tryptic soy broth, approximately 4 grams of inulin, approximately 0.4 grams of cysteine, and approximately 3.6 milliliters of 50% glycerol in approximately 900 milliliters of water. Such a growth broth may be kept and/or used in a sealed one liter bottle. Such a growth broth may be used to grow a probiotic organism, for example and not by way of limitation, *Bacteroides thetaiotaomicron.*

In one embodiment, a growth broth, or liquid growth medium, may be comprised of approximately 26 grams of tryptic soy broth, approximately 4 grams of inulin, approximately 2.5 grams of Middlebrook 7H9 broth, and approximately 7.2 milliliters of 50% glycerol in approximately 900 milliliters of water. Such a growth broth may be kept and/or used in a sealed one liter bottle. Such a growth broth may be used to grow a probiotic organism, for example and not by way of limitation, *Mycobacterium vaccae.* This probiotic organism may be grown aerobically.

In one embodiment, a growth broth, or liquid growth medium, may be comprised of approximately 50 grams of MRS broth, approximately 0.1 grams of glutathione, approximately 0.4 grams of cysteine, and approximately 0.2 grams of uric acid in approximately 900 milliliters of water. Such a growth broth may be kept and/or used in a sealed one liter bottle. Such a growth broth may be used to grow a probiotic organism, for example and not by way of limitation, *Collinsella aerofaciens.*

In one embodiment, a growth broth, or liquid growth medium, may be comprised of approximately 50 grams of MRS broth in approximately 900 milliliters of water. Such a growth broth may be kept and/or used in a sealed one liter bottle. Such a growth broth may be used to grow a probiotic organism, for example and not by way of limitation, *Pediococcus acidilactici, Lactobacillus farciminis,* and *Lactobacillus vaginalis.* These probiotic organisms may be grown aerobically or anaerobically.

In one embodiment, a growth broth, or liquid growth medium, may be comprised of approximately 33 grams of brain heart infusion, approximately 0.1 grams of glutathione, approximately 0.4 grams of cysteine, approximately 8 grams of inulin, approximately 4.5 grams of yeast extract, and approximately 1.8 grams of sodium acetate in approximately 900 milliliters of water. Such a growth broth may be kept and/or used in a sealed one liter bottle. Such a growth broth may be used to grow a probiotic organism, for example and not by way of limitation, *Faecalibacterium prausnitzii.*

In one embodiment, a growth broth, or liquid growth medium, may be comprised of approximately 7 grams of nutrient broth, approximately 4.5 grams of tryptone, approximately 9 grams of yeast extract, approximately 8 grams of inulin, approximately 4.5 grams of dextrose, approximately 1.5 grams of dipotassium phosphate (K$_2$HPO$_4$), approximately 4.5 milliliters of 20% tween 80, approximately 0.4 grams of cysteine, and approximately 27 milliliters of a salt solution in approximately 900 milliliters of water. The salt solution may be comprised of approximately 0.2 grams of calcium chloride (CaCl$_2$), approximately 0.24 grams of magnesium sulfate (MgSO$_4$), approximately 1.0 grams of monopotassium phosphate (KH$_2$PO$_4$), approximately 10 grams of sodium bicarbonate (NaHCO$_3$), and approximately 2.0 grams of sodium chloride (NaCl) in approximately one liter of water. Such a growth broth may be kept and/or used in a sealed one liter bottle. Such a growth broth may be used to grow a probiotic organism, for example and not by way of limitation, *Eubacterium rectale, Anaerostipes caccae*, and *Butyricicoccus pullicaecorum*.

In one embodiment, a growth broth, or liquid growth medium, may be comprised of approximately 7 grams of nutrient broth, approximately 4.5 grams of tryptone, approximately 9 grams of yeast extract, approximately 8 grams of inulin, approximately 4.5 grams of dextrose, approximately 1.5 grams of dipotassium phosphate (K$_2$HPO$_4$), approximately 4.5 milliliters of 20% tween 80, approximately 0.4 grams of cysteine, approximately 0.1 grams of glutathione, and approximately 27 milliliters of a salt solution in approximately 900 milliliters of water. The salt solution may be comprised of approximately 0.2 grams of calcium chloride (CaCl$_2$), approximately 0.24 grams of magnesium sulfate (MgSO$_4$), approximately 1.0 grams of monopotassium phosphate (KH$_2$PO$_4$), approximately 10 grams of sodium bicarbonate (NaHCO$_3$), and approximately 2.0 grams of sodium chloride (NaCl) in approximately one liter of water. Such a growth broth may be kept and/or used in a sealed one liter bottle. Such a growth broth may be used to grow a probiotic organism, for example and not by way of limitation, *Eubacterium rectale* and *Anaerostipes caccae*.

In one embodiment, a growth broth, or liquid growth medium, may be comprised of approximately 7 grams of nutrient broth, approximately 4.5 grams of tryptone, approximately 9 grams of yeast extract, approximately 8 grams of inulin, approximately 4.5 grams of dextrose, approximately 1.5 grams of dipotassium phosphate (K$_2$HPO$_4$), approximately 4.5 milliliters of 20% tween 80, approximately 0.4 grams of cysteine, approximately 0.1 grams of glutathione, approximately 1.8 grams of sodium acetate, approximately 0.9 grams of sodium lactate, and approximately 27 milliliters of a salt solution in approximately 900 milliliters of water. The salt solution may be comprised of approximately 0.2 grams of calcium chloride (CaCl$_2$), approximately 0.24 grams of magnesium sulfate (MgSO$_4$), approximately 1.0 grams of monopotassium phosphate (KH$_2$PO$_4$), approximately 10 grams of sodium bicarbonate (NaHCO$_3$), and approximately 2.0 grams of sodium chloride (NaCl) in approximately one liter of water. Such a growth broth may be kept and/or used in a sealed one liter bottle. Such a growth broth may be used to grow a probiotic organism, for example and not by way of limitation, *Anaerostipes caccae, Eubacterium hallii, Intestinibacter bartlettii*, and *Subdoligranulum variabile*.

In one embodiment, a growth broth, or liquid growth medium, may be comprised of approximately 7 grams of nutrient broth, approximately 4.5 grams of tryptone, approximately 9 grams of yeast extract, approximately 8 grams of inulin, approximately 4.5 grams of dextrose, approximately 1.5 grams of dipotassium phosphate (K$_2$HPO$_4$), approximately 4.5 milliliters of 20% tween 80, approximately 0.4 grams of cysteine, approximately 0.1 grams of glutathione, approximately 0.2 grams of ammonium sulfate, and approximately 27 milliliters of a salt solution in approximately 900 milliliters of water. The salt solution may be comprised of approximately 0.2 grams of calcium chloride (CaCl$_2$), approximately 0.24 grams of magnesium sulfate (MgSO$_4$), approximately 1.0 grams of monopotassium phosphate (KH$_2$PO$_4$), approximately 10 grams of sodium bicarbonate (NaHCO$_3$), and approximately 2.0 grams of sodium chloride (NaCl) in approximately one liter of water. Such a growth broth may be kept and/or used in a sealed one liter bottle. Such a growth broth may be used to grow a probiotic organism, for example and not by way of limitation, *Dorea longicatena*.

In one embodiment, a growth broth, or liquid growth medium, may be comprised of approximately 33 grams of brain heart infusion, approximately 1.0 grams of mucin, and approximately 0.4 grams of cysteine in approximately 900 milliliters of water. Such a growth broth may be kept and/or used in a sealed one liter bottle. Such a growth broth may be used to grow a probiotic organism, for example and not by way of limitation, *Akkermansia muciniphila*.

In one embodiment, a growth broth, or liquid growth medium, may be comprised of approximately 27 grams of tryptic soy broth, approximately 4 grams of yeast extract, approximately 0.8 grams of sodium lactate, approximately 0.4 grams of magnesium sulfate, approximately 0.3 grams of ferric ammonium sulfate-6H$_2$O, approximately 0.4 grams of cysteine, and approximately 0.1 grams of glutathione in approximately 900 milliliters of water. Such a growth broth may be kept and/or used in a sealed one liter bottle. Such a growth broth may be used to grow a probiotic organism, for example and not by way of limitation, *Desulfovibrio piger*.

In one embodiment, a growth broth, or liquid growth medium, may be comprised of approximately 50 grams of MRS broth, approximately 0.4 grams of cysteine, approximately 0.1 grams of glutathione, and approximately 27 milliliters of a salt solution in approximately 900 milliliters of water. The salt solution may be comprised of approximately 0.2 grams of calcium chloride (CaCl$_2$), approximately 0.24 grams of magnesium sulfate (MgSO$_4$), approximately 1.0 grams of monopotassium phosphate (KH$_2$PO$_4$), approximately 10 grams of sodium bicarbonate (NaHCO$_3$), and approximately 2.0 grams of sodium chloride (NaCl) in approximately one liter of water. Such a growth broth may be kept and/or used in a sealed one liter bottle. Such a growth broth may be used to grow a probiotic organism, for example and not by way of limitation, *Roseburia hominis*.

In one embodiment, a growth broth, or liquid growth medium, may be comprised of approximately 7 grams of nutrient broth in approximately 900 milliliters of water. Such a growth broth may be kept and/or used in a sealed one liter bottle. Such a growth broth may be used to grow a probiotic organism, for example and not by way of limitation, *Roseomonas mucosa*. This probiotic may be grown aerobically.

In one embodiment, a growth broth, or liquid growth medium, may be comprised of approximately 7 grams of nutrient broth and approximately 4.5 grams of dextrose in approximately 900 milliliters of water. Such a growth broth may be kept and/or used in a sealed one liter bottle. Such a growth broth may be used to grow a probiotic organism, for example and not by way of limitation, *Roseomonas mucosa*. This probiotic may be grown aerobically.

In one embodiment, a growth broth, or liquid growth medium, may be comprised of approximately 27 grams of tryptic soy broth in approximately 900 milliliters of water. Such a growth broth may be kept and/or used in a sealed one liter bottle. Such a growth broth may be used to grow a probiotic organism, for example and not by way of limitation, *Staphylococcus epidermidis*. This probiotic organism may be grown aerobically or anaerobically.

In one embodiment, a growth broth, or liquid growth medium, may be comprised of approximately 27 grams of tryptic soy broth and approximately 7.2 milliliters of 50% glycerol in approximately 900 milliliters of water. Such a growth broth may be kept and/or used in a sealed one liter bottle. Such a growth broth may be used to grow a probiotic organism, for example and not by way of limitation, *Staphylococcus epidermidis*. This probiotic organism may be grown aerobically or anaerobically.

In one embodiment, a growth broth, or liquid growth medium, may be comprised of approximately 27 grams of tryptic soy broth and approximately 7.2 milliliters of 50% glycerol in approximately 900 milliliters of water. Such a growth broth may be kept and/or used in a sealed one liter bottle. Such a growth broth may be used to grow a probiotic organism, for example and not by way of limitation, *Staphylococcus xylosus*. This probiotic organism may be grown aerobically or anaerobically.

In one embodiment, an agar spread plate media, or agar spread plate, may be comprised of approximately 40 g/L tryptic soy agar, approximately 50 ml/L defibrinated sheep blood, approximately 0.5 g/L cysteine, and approximately 0.1 g/L glutathione. Such an agar spread plate may be used to grow a probiotic organism, for example and not by way of limitation, *Bacteroides thetaiotaomicron, Bacteroides fragilis, Bacteroides ovatus, Bacteroides uniformis, Eubacterium limosum, Clostridium symbiosum, Collinsella aerofaciens, Faecalibacterium prausnitzii, Eubacterium rectale, Roseburia hominis, Anaerostipes caccae, Butyricicoccus pullicaecorum, Roseomonas mucosa, Staphylococcus epidermidis, Staphylococcus xylosus, Eubacterium hallii, Dorea longicatena, Intestinibacter bartlettii*, and *Subdoligranulum variabile*.

In one embodiment, an agar spread plate media, or agar spread plate, may be comprised of approximately 12 g/L agar and a growth broth (approximately 3 g/L) comprised of approximately 26 grams of tryptic soy broth, approximately 4 grams of inulin, approximately 2.5 grams of Middlebrook 7H9 broth, and approximately 7.2 milliliters of 50% glycerol in approximately 900 milliliters of water. Such an agar spread plate may be used to grow a probiotic organism, for example and not by way of limitation, *Mycobacterium vaccae*. This probiotic organism may be grown aerobically.

In one embodiment, an agar spread plate media, or agar spread plate, may be comprised of approximately 70 g/L of MRS agar. Such an agar spread plate may be used to grow a probiotic organism, for example and not by way of limitation, *Pediococcus acidilactici, Lactobacillus farciminis*, and *Lactobacillus vaginalis*. These probiotic organisms may be grown aerobically or anaerobically.

In one embodiment, an agar spread plate media, or agar spread plate, may be comprised of approximately 12 g/L agar and a growth broth (approximately 3 g/L) comprised of approximately 33 grams of brain heart infusion, approximately 1.0 grams of mucin, and approximately 0.4 grams of cysteine in approximately 900 milliliters of water. A pour plate may use 8 g/L agar. Such an agar spread plate may be used to grow a probiotic organism, for example and not by way of limitation, *Akkermansia muciniphila*.

In one embodiment, an agar spread plate media, or agar spread plate, may be comprised of approximately 10 g/L agar and a growth broth (approximately 3 g/L) comprised of approximately 27 grams of tryptic soy broth, approximately 4 grams of yeast extract, approximately 0.8 grams of sodium lactate, approximately 0.4 grams of magnesium sulfate, approximately 0.3 grams of ferric ammonium sulfate-$6H_2O$, approximately 0.4 grams of cysteine, and approximately 0.1 grams of glutathione in approximately 900 milliliters of water. A pour plate may use 10 g/L agar. Such an agar spread plate may be used to grow a probiotic organism, for example and not by way of limitation, *Desulfovibrio piger*.

In one embodiment, an agar spread plate media, or agar spread plate, may be comprised of approximately 52.5 g/L of reinforced clostridial agar in approximately 900 milliliters of water. A pour plate may use 10 g/L agar. Such an agar spread plate may be used to grow a probiotic organism, for example and not by way of limitation, *Parabacteroides distasonis*, and *Parabacteroides goldsteinii*.

In one embodiment, a freeze-drying buffer, or lyophilization buffer, may be used to freeze-dry probiotic organisms that are grown and harvested. Freeze-drying reagents, or lyophilization reagents, may include the following compounds alone or in combination: glucosamine, sucrose, mannitol, trehalose, glycerol, inositol, raffinose, inulin, powdered skim milk, activated charcoal, soluble starch, collagen powder, chondroitin sulfate, glucosamine sulfate, glutamine, guar, acacia, silica, and fructooligiosaccharide P95. A freeze-drying buffer, or lyophilization buffer, may be comprised of appropriate amounts of one or more of the freeze-drying reagents in deionized water, which is then adjusted to a pH of 7.0 with potassium hydroxide.

In one embodiment, a freeze-drying buffer may be made at least one day prior to the freeze-drying process. A freeze-drying buffer may be stored overnight in an anaerobic chamber to allow dissolved oxygen to escape the solution. The volume of a freeze-drying buffer used may be equal to the volume of a cell pellet or probiotic organisms obtained after centrifugation.

In one embodiment, a freeze-drying buffer or media may be made with anti-oxidant and growth factors, for example and not by way of limitation, cysteine, ascorbic acid, glutathione, uric acid, riboflavin, glutamic acid, sodium sulfite, quinones, alpha lipoic acid, resveratrol, vitamin A, and vitamin E.

In one embodiment, a freeze-drying buffer, or lyophilization buffer, may be comprised of 10% mannitol, 12.5% sucrose, 2.5% trehalose, 1.0% glycerol, 10% skim milk, 0.02% cysteine, 0.01% ascorbic acid, 0.005% glutathione, 0.005% uric acid, and 2.0% charcoal in deionized water and adjusted to pH 7 with potassium hydroxide. The percentages provided may be considered approximate percentages. This embodiment of a freeze-drying buffer will hereinafter be referred to as "Freeze-drying Buffer A." Freeze-drying Buffer A may be used with various probiotic organisms, for example and not by way of limitation, *Mycobacterium vaccae, Pediococcus acidilactici, Roseomonas mucosa, Lactobacillus farciminis, Lactobacillus vaginalis, Staphylococcus epidermidis*, and *Staphylococcus xylosus*.

In one embodiment, a freeze-drying buffer, or lyophilization buffer, may be comprised of 10% mannitol, 12.5% sucrose, 2.5% trehalose, 1.0% glycerol, 10% skim milk, 0.2% cysteine, 0.1% ascorbic acid, 0.05% glutathione, 0.05% uric acid, and 2.0% charcoal in deionized water and adjusted to pH 7 with potassium hydroxide. The percentages provided may be considered approximate percentages. This embodiment of a freeze-drying buffer will hereinafter be referred to as "Freeze-drying Buffer B." Freeze-drying Buffer B may be used with various probiotic organisms, for example and not by way of limitation, *Bacteroides thetaiotaomicron, Bacteroides fragilis, Bacteroides ovatus,*

*Bacteroides uniformis, Eubacterium limosum, Collinsella aerofaciens, Akkermansia muciniphila,* and *Roseburia hominis.*

In one embodiment, a freeze-drying buffer, or lyophilization buffer, may be comprised of 10% mannitol, 10% inulin, 5% short chain FOS, 10% soluble starch, 2.5% trehalose, 1.0% glycerol, 2.0% cysteine, 0.5% ascorbic acid, 0.5% glutathione, 0.1% uric acid, and 6.0% charcoal in deionized water and adjusted to pH 7 with potassium hydroxide. The percentages provided may be considered approximate percentages. This embodiment of a freeze-drying buffer will hereinafter be referred to as "Freeze-drying Buffer C." Freeze-drying Buffer C may be used with various probiotic organisms, for example and not by way of limitation, *Clostridium symbiosum, Faecalibacterium praunsnitzii, Eubacterium rectale, Anaerostipes caccae, Butyricicoccus pullicaecorum, Eubacterium hallii, Dorea longicatena, Parabacteroides distasonis, Parabacteroides goldsteinii, Intestinibacter bartettii,* and *Subdoligranulum variable.*

In one embodiment, a freeze-drying buffer, or lyophilization buffer, may be comprised of 10% mannitol, 12.5% sucrose, 2.5% trehalose, 10% collagen powder, 1.0% chondroitin sulfate, 1.0% glycerol, 2.0% cysteine, 0.5% ascorbic acid, 0.5% glutathione, 0.1% uric acid, and 6.0% charcoal in deionized water and adjusted to pH 7 with potassium hydroxide. The percentages provided may be considered approximate percentages. This embodiment of a freeze-drying buffer will hereinafter be referred to as "Freeze-drying Buffer D." Freeze-drying Buffer D may be used with various probiotic organisms, for example and not by way of limitation, *Desulfovibrio piger.*

In one embodiment, a freeze-drying buffer, or lyophilization buffer, may be comprised of 10% mannitol, 10% inulin, 5% short chain FOS, 10% soluble starch, 2.5% trehalose, 1% glycerol, 5% cysteine, 1% ascorbic acid, 5% glutathione, 1% uric acid, 1% alpha lipoic acid, 1% resveratol, and 6.0% charcoal in deionized water and adjusted to pH 7 with potassium hydroxide. The percentages provided may be considered approximate percentages. This embodiment of a freeze-drying buffer will hereinafter be referred to as "Freeze-drying Buffer E." Freeze-drying Buffer E may be used with various probiotic organisms, for example and not by way of limitation, *Faecalibacterium prausnitzii.*

In one embodiment, a dilution buffer, or anti-oxidant resuspension solution, may be utilized for plating lyophilized bacteria and/or obtaining plate counts and estimating cfu/gram (colony-forming unit per gram of sample). In one embodiment, a dilution buffer, or anti-oxidant resuspension solution, may be comprised of 0.2% cysteine, 0.1% ascorbic acid, 0.05% glutathione, 0.05% uric acid, and 0.0425% monopotassium phosphate ($KH_2PO_4$) monopotassium phosphate ($KH_2PO_4$) in deionized water and adjusted to pH 7 with potassium hydroxide solution.

Culture conditions for various probiotic organisms have been determined experimentally.

In one embodiment, various probiotic organisms, for example and not by way of limitation, *Bacteroides thetaiotaomicron, Bacteroides fragilis, Bacteroides ovatus, Bacteroides uniformis, Eubacterium limosum, Collinsella aerofaciens, Akkermansia muciniphila, Anaerostipes caccae,* and *Desulfovibrio piger* require 48-96 hours of incubation at 37° C. to achieve the desired growth. The addition of anti-oxidants during media preparation may be required, but no special anaerobic conditions are required for growth in liquid media, or growth broth. The liquid media bottles should be capped to prevent contamination and to limit airflow to the growing probiotic cultures. Disturbance of the liquid media, such as swirling, should be avoided to limit oxygen rich air being mixed with the liquid media.

Centrifugation and freeze-drying processes can be performed in an aerobic environment if done quickly, for example, by mixing the centrifuged pellet with a freeze-dry buffer immediately after pouring off the supernatant and then placing the suspension at −20° C. It may take approximately one hour to fully freeze the suspension. Then the suspension can be placed in the lyophilizer.

Spread plating or pour plating techniques can be used for these probiotic organisms, provided that the dilution buffer, or antioxidant resuspension solution, is used. Plates should be put in an anaerobic chamber or airtight box containing anaerobic gas producing packets. Growth of colonies on plates typically requires 24-72 hours at 37° C.

In one embodiment, various probiotic organisms, for example and not by way of limitation, *Clostridium symbiosum, Faecalibacterium prausnitzii, Eubacterium rectale, Roseburia hominis, Anaerostipes caccae, Butyricicoccus pullicaecorum, Eubacterium hallii, Dorea longicatena, Parabacteroides distasonis, Parabacteroides goldsteinii, Intestinibacter bartettii,* and *Subdoligranulum variable* require 24-48 hours of incubation at 37° C. to achieve desired growth. These probiotic organisms grow poorly unless incubated in an oxygen-free environment. Oxygen rich air must be evacuated from liquid media bottles before placing them in an anaerobic chamber.

For centrifugation, liquid cultures must be poured into airtight centrifuge bottles and sealed in an anaerobic chamber. The centrifuge bottles can then be removed from the chamber to undergo centrifugation. They must be placed back in the anaerobic chamber before opening to pour off the supernatant. The cell pellets are then suspended in freeze-dry buffer that has been sitting in the anaerobic chamber overnight, or for approximately twelve hours, to help pull off oxygen dissolved in the buffer. The cell suspension is then sealed in an airtight container and placed at −20° C. until lyophilized in aerobic conditions.

All plating techniques must be performed in the anaerobic chamber. Growth of colonies on plates typically requires 24-48 hours at 37° C.

In one embodiment, various probiotic organisms, for example and not by way of limitation, *Mycobacterium vaccae, Pediococcus acidilactici, Roseomonas mucosa, Lactobacillus farciminis, Lactobacillus vaginalis, Staphylococcus epidermidis,* and *Staphylococcus xylosus* require 24-48 hours of incubation at 37° C. to achieve desired growth, except that *M. vaccae* may require 5-8 days. These probiotic organisms may be cultured aerobically. Aeration of liquid media, or growth broth, using a stir plate and a stir bar improves growth of *M. vaccae, R. mucosa, S. epidermidis,* and *S. xylosus.*

Centrifugation, any freeze-drying process, and plate growth techniques may all occur in an aerobic environment. Colonies on plates are typically observed in 24-48 hours at 37° C., except that *M. vaccae* may take 3-5 days.

Prebiotic formulations may be used to supplement, support, and optimize probiotic growth, which process may be referred to as synbiotics. In order to facilitate growth of a given probiotic organism, the correct or matching prebiotic is crucial. Since probiotic organisms vary in genus and species, specific prebiotic preparations or formulations may be required. Some prebiotics colonize the lumen and others the mucus layers. Many prebiotics are butyrate-producing *Firmicutes* members.

Prebiotics often enhance mucosal butyrate, which has been shown to possibly stimulate the release of mucosal butyrate producers towards the lumen. A process connected with that may affect the intestinal inflammation and consumption of prebiotic compounds.

Some probiotic organisms require other special conditions like co-culturing with another commensal organism. For example and not by way of limitation, *Bacteroides fragilis* produces GABA (Gamma-Aminobutyric Acid), a metabolite required by a second organism. Therefore, the two organisms may be considered co-dependent.

Various techniques may be utilized to introduce a prebiotic, or a prebiotic formulation, to a method for growing a certain probiotic organism, or multiple probiotic organisms. In one embodiment, a growth media may be exogenously supplemented with the needed metabolite. In another embodiment, the supernatant of one organism may be used to supplement the growth media used for growing another organism of interest. For example and not by way of limitation, growth of *Faecalibacterium prausnitzii* may require special supplementation of one or more specific vitamin K metabolites.

Table 1 below describes a prebiotic formulation that may be used with probiotic organisms including *Faecalibacterium prausnitzii, Mycobacterium vaccae*, and *Lactobacillus farciminis*.

TABLE 1

| Prebiotic | mg/ser |
|---|---|
| Galacto-oligosaccharide | 3000.0 |
| Isomalt-oligosaccharide | 3000.0 |
| IgY-immunoglobulin | 100.0 |
| Deoxynojirimycin polysaccharide (DPM) | 500.0 |
| Lactoferrin | 50.0 |
| Guggulipids | 500.0 |
| Sorghum | 2000.0 |
| Pectin | 1000.0 |
| Fructooligosaccharide (FOS) | 1000.0 |
| Blueberry powder | 1000.0 |
| Black currant | 1000.0 |
| Lions mane mushroom | 500.0 |
| Cordyceps militarus | 500.0 |
| Karaya gum | 500.0 |
| Pomegranate (ellagitanin) | 500.0 |
| Geranium thunbergii (dehydroellagitanin) | 500.0 |
| Phyllanthus muellerianus (Geraniin and furosin) | 500.0 |
| Raspberry extract (gallic ellagic) | 500.0 |
| Total | 16650.0 |

The amounts in Table 1 may be considered approximations. The prebiotic formulation represented in Table 1 may be hereinafter referred to as "Prebiotic Formula Alpha."

Table 2 below describes a prebiotic formulation that may be used with probiotic organisms including *Eubacterium limosum, Bacteroides thetaiotaomicron, Lactobacillus vaginalis*, and *Bacteroides uniformis*.

TABLE 2

| Prebiotic | mg/ser |
|---|---|
| Glycomacropeptide | 1000.0 |
| Xylo-oligosaccharide | 1000.0 |
| Glucomannan | 1000.0 |
| Inulin; sprouted greens | 1000.0 |
| Galactomannan | 1000.0 |
| Blueberry powder | 1000.0 |
| Thymus | 1000.0 |
| Mulberry leaves | 1000.0 |
| Myo-inositol | 1000.0 |
| Modified citrus pectin | 1000.0 |
| Tapioca | 500.0 |

TABLE 2-continued

| Prebiotic | mg/ser |
|---|---|
| Glucosaminoglycan | 1000.0 |
| Guar sun-fiber | 500.0 |
| Oat oligosaccharide | 500.0 |
| Clitoria ternatea (blue pea flower) | 500.0 |
| Cranberry extract | 500.0 |
| Bearberry (*Arctostaphylos uva-ursi*) | 500.0 |
| Total | 14000.0 |

The amounts in Table 2 may be considered approximations. The prebiotic formulation represented in Table 2 may be hereinafter referred to as "Prebiotic Formula Beta."

Table 3 below describes a prebiotic formulation that may be used with probiotic organisms including *Bacteroides ovatus, Anaerostipes caccae, Staphylococcus xylosus, Staphylococcus epidermidis*, and *Roseomonas mucosa*.

TABLE 3

| Prebiotic | mg/ser |
|---|---|
| 2'fructosyllactose | 2000.0 |
| Isomato-oligosaccharide | 1000.0 |
| Fructooligosaccharide Yacon root/Beneo/innulin | 1000.0 |
| Galactooligosaccharide | 1000.0 |
| Rutin | 1000.0 |
| Oat oligosaccharide | 1000.0 |
| Sialylated bovine milk oligosaccharides (S-BMO) | 1000.0 |
| IgY immunoglobulin | 1000.0 |
| Beta glucan | 1000.0 |
| Maca | 1000.0 |
| Lactooligosaccharide | 1000.0 |
| Medium Chain Triglycerides | 500.0 |
| Phosphatidyl choline | 500.0 |
| Rose hips/organic green banana | 500.0 |
| Citrus bioflavonoids | 500.0 |
| Colostrum | 500.0 |
| Total | 14500.0 |

The amounts in Table 3 may be considered approximations. The prebiotic formulation represented in Table 3 may be hereinafter referred to as "Prebiotic Formula Gamma."

Table 4 below describes a prebiotic formula that may be used with probiotic organisms including *Collinsella aerofaciens, Bacteroides ovatus, Bacteroides uniformis, Clostridium symbiosum, Bacteroides fragilis*, and *Roseburia hominis*.

TABLE 4

| Prebiotic | mg/ser |
|---|---|
| Galacto-oligosaccharide | 2000.0 |
| Mannan-oligosaccharide | 1000.0 |
| Resveratrol | 1000.0 |
| Hesperetin | 1000.0 |
| Arabinoxylan oligosaccharides | 1000.0 |
| Dragon fruit | 1000.0 |
| Beechwood extract xylan | 1000.0 |
| Arabinogalactan (*Larix laricina*) | 1000.0 |
| DAO antihistamine | 1000.0 |
| Xanthan gum | 1000.0 |
| Resistant starch | 1000.0 |
| Baobab fruit | 500.0 |
| Kongorobi berry | 1000.0 |
| Resveratrol/Pterostilbene | 500.0 |
| Curcumin | 500.0 |
| Indian Tinospora (*Tinospora cordifolia*)(stem and root) | 500.0 |
| Poria mushroom | 500.0 |
| Total | 15500.0 |

The amounts in Table 4 may be considered approximations. The prebiotic formulation represented in Table 4 may be hereinafter referred to as "Prebiotic Formula Delta."

The various prebiotic formulations may be utilized with a liquid media or growth broth. The prebiotic formulation selected and paired with a given probiotic organism may constitute approximately 1%-15% of the growth broth. Similarly, the various prebiotic formulations may be utilized with an agar spread plate. The prebiotic formulation selected and paired with a given probiotic organism may constitute approximately 1%-15% of the agar spread plate media.

Prebiotic ingredients used in prebiotic formulations can many different types of compounds. For example and not by way of limitation, complex plant oligosaccharides may include the following: Galacto-oligosaccharide; Isomalt-oligosaccharide; Mannan-oligosaccharide; Apple pectin oligosaccharide; Xylo-oligosaccharide; and Fructo-oligosaccharide-inulin. These complex plant oligosaccharides have been shown increase caecal mucin levels by approximately six-fold and correspond with even higher butyrate levels and higher abundances of the same mucosal butyrate producers.

Other complex plant oligosaccharides include Oat-oligosaccharides and Arabinoxylan-oligosaccharides (AXOS), which have been shown to be a promising class of prebiotics that stimulate the growth of *Bifidobacterium longum*, an acetate producer to stimulate *Eubacterium rectale*, an acetate-converting butyrate producer.

Another complex plant oligosaccharide is Deoxynojirimycin polysaccharide (DPM), which has been shown to increase the *Bacteroides* to *Firmicutes* ratios, significantly inhibiting the growth of *Prevotella*, and increasing the relative abundance of *Bacteroides, Lactobacillus, Bifidobacterium*, and *Akkermansia* in mice.

Animal based oligosaccharides may include the following: N-acetyl glucosamine-amino glycan Lactulose-saccharide; IgY-immunoglobulin; and Sialylated bovine milk oligosaccharides (S-BMO).

Other complex prebiotic compounds may include the following: Cyclodextrin-saccharide; Mulberry-cyanadins; Maca-oligosaccharides; polyphenols; Rutin-flavonoid (*E. limosum* specifically metabolized flavonoids); mushroom-polysaccharides; aminoglycans; Shilajit (organic compounds); Resveratrol; and Pterostilbene.

The criteria for pairing or partnering certain probiotic organisms with specific prebiotics is driven by the metabolites that are produced by the probiotic organisms. For example and not by way of limitation, the metabolites produced by probiotic organisms that may be evaluated to pair or partner those probiotic organisms with specific prebiotics may include the following: small chain fatty acids, such as butyric acid, acetic acid, propionic acid, hexanoic acid, and the like; organic acids, such as lactic acid, malic acid, citric acid, and the like; bacteriocins, which are natural antimicrobials produced by probiotic organisms. The research and analysis required to properly partner probiotic organisms and prebiotic compounds can take years to complete.

FIG. 1 provides an example of the research conducted and evaluated to properly partner probiotic organisms and prebiotic compounds based on the production of short chain fatty acids produced in selected strains of probiotic organisms. The values for short chain fatty acids in FIG. 1 are in milligrams per milliliter measured from culture supernatant.

In one embodiment, a phage may be used as a terrain biotic. For example and not by way of limitation, terrain biotics may include *Streptococcus mutans, Actinomyces naeslundi, Cutibacterium acnes, Porphyromonas gingivalis,* *Treponema denticola, Fusobactium nucleatum, Aggregatibacter actinomycetemcomitans,* and *Tannerella forsythia*.

Referring to FIG. 2, one embodiment of a method 10 for producing probiotic organisms may include the steps of selecting a probiotic organism to grow 15, selecting a prebiotic formula 20 to pair with the probiotic organism selected, selecting a growth broth 25, inoculating the growth broth 30, growing the probiotic organism 35, harvesting the probiotic organism from the growth broth 40, selecting a growth plate 45, inoculating the growth plate 50, growing the probiotic organism on the growth plate 55, harvesting the probiotic organism from the growth plate 60, and freeze-drying the probiotic organism 65.

The step of selecting a probiotic organism to grow 15 can be based on numerous factors. The uses, properties, and metabolites of a given probiotic organism may be considered. Generally, the process of beginning to grow a probiotic organism will start with a pure strain of the organism, but it is possible to grow multiple probiotic organisms together. However, more care should be taken to select organisms that can be grown using the same growth media, as well as the same prebiotic formulations, to optimize growth of all probiotic organisms selected.

The step of selecting a prebiotic formula, or formulation, 20 to grow the selected probiotic organism should be based primarily on the probiotic organism selected. The intention is to match or partner the prebiotics with the probiotic organism as best as can be done to promote optimal growth of the probiotic organism. For example and not by way of limitation, if *Mycobacterium vaccae* is the probiotic organism selected to be grown, Prebiotic Formula Alpha would be an optimal choice for prebiotics to pair with the probiotic organism during the growth process.

The step of selecting a growth broth 25, or selecting a liquid media for growth 25, may include a number of factors. A growth broth can be selected based on the particular probiotic organism to be grown, and there are certain growth broths that can be used to grow specific probiotic organisms. Also, a growth broth may include at least some of a prebiotic formulation to promote the growth process. A growth broth may be augmented to include a prebiotic formula where the prebiotic formula is approximately 1%-15% of the growth broth media. For example and not by way of limitation, if *Bacteroides fragilis* is the probiotic organism to be grown, the growth broth used (and previously described) may be augmented to be approximately 10% Prebiotic Formula Delta.

The step of inoculating the growth broth 30 is generally performed by introducing the selected probiotic organism into the selected and prepared growth broth by any appropriate means.

The step of growing the probiotic organism in the growth broth 35 is accomplished by any appropriate means. For example and not by way of limitation, if *Bacteroides fragilis* is the probiotic organism to be grown, the growth broth may be kept in a sealed bottle and allowed to incubate for 48-96 hours at 37° C. For example and not by way of limitation, if *Mycobacterium vaccae* is the probiotic organism to be grown, the growth should take place anaerobically.

The step of harvesting the probiotic organism from the growth broth 40 is generally accomplished by any appropriate means that are consistent with the requirements for the probiotic organism. For example and not by way of limitation, if *Mycobacterium vaccae* is the probiotic organism to be grown, this harvesting process should take place anaerobically.

The step of selecting a growth plate 45, or selecting an agar spread plate for growing the selected probiotic organism 45, may include consideration of multiple factors. The type of media used for the growth plate should be compatible with the probiotic organism to be grown. Also, the media of the growth plate may include a prebiotic formulation to promote growth of the probiotic organism. For example and not by way of limitation, if *Bacteroides thetaiotaomicron* is the probiotic organism to be grown, the growth plate used, or agar spread plate used (and previously described), may be augmented to include approximately 5% Prebiotic Formula Beta.

The step of inoculating the growth plate 50, or inoculating and/or preparing the agar spread plate 50, is generally performed by introducing the probiotic organism harvested from the growth broth 40 onto the surface of the selected and prepared growth plate by any appropriate means. For example and not by way of limitation, if *Roseburia hominis* is the probiotic organism to be grown, the inoculating and/or preparing the growth plate should take place anaerobically.

The step of growing the probiotic organism on the growth plate 55, or growing the probiotic organism on the agar spread plate 55, is accomplished by any appropriate means. For example and not by way of limitation, if *Bacteroides fragilis* is the probiotic organism to be grown, the growth plate may be allowed to incubate for 24-72 hours at 37° C. For example and not by way of limitation, if *Mycobacterium vaccae* is the probiotic organism to be grown, the growth should take place anaerobically.

The step of harvesting the probiotic organism from the growth plate 60 is generally accomplished by any appropriate means that are consistent with the requirements for the probiotic organism. For example and not by way of limitation, if *Mycobacterium vaccae* is the probiotic organism to be grown, this harvesting process should take place anaerobically.

The step of freeze-drying the probiotic organism 65 may include consideration of a variety of factors. There may be times when the freeze-drying step is not required or desired. The probiotic organism may require preparation for storage and/or delivery. Also, a specially prepared buffer for the freeze-dry process, or freeze-drying buffer, may be utilized for lyophilization of a specific probiotic organism. For example and not by way of limitation, if *Clostridium symbiosum* is the probiotic organism that has been grown, then Freeze-drying Buffer C may be used to more appropriately freeze-dry that probiotic organism.

Similar to how there are numerous, possible combinations of probiotics with suitable or optimal prebiotics, there are also numerous, possible combinations of probiotics that can be used to help with or benefit selected physiological functions. Moreover, each probiotic selected for such a combination can be accompanied by its most advantageous prebiotics. For example, one or more probiotics can be selected for and provided in a product for supporting neurological functions, immune system functions, female functions, male functions, and metabolic functions, as well as others.

Certain microorganisms are capable of influencing the central nervous system. This process is sometimes described as the "microbiota-gut-brain axis." There are a number of mechanisms that have been identified as mediating this phenomenon, including the vagal nerve, the immune system, and neurotransmitters. There may be a number of links between the gastro-intestinal microbiome and the brain related to important physiological functions, including neurotransmitter production, enteric nervous system hormones, central nervous system development, mood, anxiety, stress and others.

In one embodiment, a combination of cultured organisms designed to benefit the health of the microbiota-gut-brain axis may include one or more of the following probiotic organisms: *Enterococcus faecium, Bifidobacterium adolescentis, Faecalibacterium prausnitzii, Mycobacterium vaccae, Lactobacillus plantarum, Bifidobacterium longum, Bifidobacterium bifidum, Lactobacillus acidophilus, Lactobacillus casei, Lactobacillus salivarius, Lactobacillus gasseri, Lactobacillus farciminis, Propionibacterium shermanii, Bifidobacterium infantis, Lactobacillus helveticus, Lactobacillus bulgaricus, Lactobacillus delbrueckii, Bacteroides fragilis, Bifidobacterium lactis*, and *Lactobacillus rhamnosus* A. These probiotic organisms may be provided in an approximate CFU range of 1.00E+06-1.00E+11.

There is a distinct advantage for these microbiota-gut-brain axis probiotic organisms if they are provided with the proper prebiotics, especially if it is desired that the probiotics remain in the gastro-intestinal tract for an extended amount of time. A prebiotic that may be used to feed these microbiota-gut-brain axis probiotic organisms is shown in Table 5.

TABLE 5

| Prebiotic | mg/dose |
| --- | --- |
| Galacto-oligosaccharide | 500-5000 |
| Isomalt-oligosaccharide/Maltosyl-isomaltooligosaccharide | 500-5000 |
| IgY-immunoglobulin | 25-500 |
| Deoxnoiirimycin polysaccharide (DPM) | 500-5000 |
| Lactoferrin | 25-500 |
| Commiphora mukul (Guggulipids) | 50-60 |
| Sorghum bicolor | 500-5000 |
| Pectin (Citrus or Rose Hips) | 500-5000 |
| FOS (fructo-oligosaccharide) | 500-5000 |
| Blueberry (Vaccinium corymbosum) powder | 500-5000 |
| Black currant (Ribes nigrum) | 500-5000 |
| Lion's mane mushroom (Hericium erinaceus) | 500-5000 |
| Cordyceps militarus | 500-5000 |
| Karaya gum (Sterculia urens) | 500-5000 |

The amounts in Table 5 may be considered approximations. The prebiotic formulation represented in Table 5 may be hereinafter referred to as "Prebiotic Formula Epsilon."

In one embodiment, the prebiotics in Table 6 may be used in vivo to support the following probiotic organisms: *Faecalibacterium prausnitzii, Mycobacterium vaccae, Lactobacillus farcimins, Parabacteroides goldsteinii*, and *Subdoligranulum variable*.

TABLE 6

| Prebiotic | mg/dose |
| --- | --- |
| Galacto-oligosaccharide | 500-5000 |
| Isomalt-oligosaccharide/Maltosyl-isomaltooligosaccharide | 500-5000 |
| IgY-immunoglobulin | 25-500 |
| Deoxnoiirimycin polysaccharide (DPM) | 500-5000 |
| Lactoferrin | 25-500 |
| Commiphora mukul (Guggulipids) | 50-60 |
| Sorghum bicolor | 500-5000 |
| Pectin (Citrus or Rose Hips) | 500-5000 |
| FOS (fructo-oligosaccharide) | 500-5000 |
| Blueberry (Vaccinium corymbosum) powder | 500-5000 |
| Black currant (Ribes nigrum) | 500-5000 |
| Lion's mane mushroom (Hericium erinaceus) | 500-5000 |
| Cordyceps militarus | 500-5000 |
| Karaya gum (Sterculia urens) | 500-5000 |
| Saffron (Crocus sativus) | 25-500 |

TABLE 6-continued

| Prebiotic | mg/dose |
| --- | --- |
| Ellagitannins-punicalagins-Pomegranate PPE (Punica granatum) | 25-500 |
| Geranium thunbergii (dehydroellagitannin) | 25-500 |
| Phyllanthus muellerianus (Geraniin and furosin) | 25-500 |
| Rasberry (Rubus idaeus) (gallic ellagic) | 25-500 |
| Gold/Green kiwi (Actinidia chinensis and Actinidia deliciosa) | 500-5000 |

The amounts in Table 6 may be considered approximations. The prebiotic formulation represented in Table 6 may be hereinafter referred to as "Prebiotic Formula Zeta."

One of the central functions of a person's microbiome is to train our immune system. The immune system is co-dependent on the microbiome for its education and its ongoing maintenance. A number of probiotic organisms have been identified as directly modulating our immune function. In one embodiment, a unique combination of probiotics may be designed around both our innate and adaptive immune systems. Proper immune modulating is dependent on prebiotics to successfully colonize the gastrointestinal tract.

In one embodiment, a combination of cultured organisms designed to benefit the health of the immune system may include one or more of the following probiotic organisms: *Bacteroides uniformis, Collinsella aerofaciens, Lactobacillus paracasei, Lactobacillus plantarum, Anerostipes caccae, Bacteroides ovatus, Clostridium symbiosum, Streptococcus thermophilus, Lactobacillus reuteri, Pediococcus pentosaceus, Lactobacillus fermentum, Saccharomyces boulardii, Bifidobacterium lactis, Bifidobacterium infantis, Bifidobacterium bifidum, Lactobacillus helveticus, Bifidobacterium longum, Roseburia hominis, Lactobacillus pentosus*, and *Lactobacillus rhamnosus*. These probiotic organisms may be provided in an approximate CFU range of 1.00E+06-1.00E+11.

In one embodiment, the prebiotics in Table 7 may be used in vivo to support the following probiotic organisms: *Bacteroides uniformis, Bacteroides ovatus, Bacteroides fragilis, Clostridium symbiosum, Collinsella aerofaciens, Roseburia hominis, Anaerostipes caccae, Pediococcus acidilactici, Butyricicoccus pullicaecorum, Roseomonas mucosa*, and *Dorea longicatena*.

TABLE 7

| Prebiotic | mg/dose |
| --- | --- |
| Bimuno-galacto-oligosaccharides (B_GOS) | 500-5000 |
| Mannan-oligosaccharide | 500-5000 |
| Resveratrol | 100-1000 |
| Hesperetin | 100-1000 |
| Arabinoxylan-oligosaccharides | 500-5000 |
| Dragon fruit | 500-5000 |
| Beechwood extract xylan | 500-5000 |
| Arabinogalactan (*Larix laricina*) | 500-5000 |
| DAO antihistamine | 500-5000 |
| Xanthan gum | 500-5000 |
| Resistant starch | 500-5000 |
| Baobab fruit | 100-500 |
| Kongorobi berry | 500-5000 |
| Resveratrol/Pterostillbene | 100-500 |
| Curcumin | 100-500 |
| Indian Tinospora (*Tinospora cordifolia*) (stem and root) | 100-500 |
| Poria mushroom | 100-500 |
| Nobiletin | 500-5000 |

The amounts in Table 7 may be considered approximations. The prebiotic formulation represented in Table 7 may be hereinafter referred to as "Prebiotic Formula Eta."

In one embodiment, a combination of cultured organisms designed to benefit the health of the adaptive immune system may include one or more of the following probiotic organisms: *Akkermansia muciniphila, Clostridium symbiosum, Bifidobacterium lactis, Collinsella aerofaciens, Bifidobacterium bifidum, Lactobacillus bulgaricus, Bacteroides fragilis, Bacteroides ovatus, Bifidobacterium animalus, Lactobacillus reuteri*, and *Lactobacillus johnsonii*. These probiotic organisms may be provided in an approximate CFU range of 1.00E+06-1.00E+11.

In one embodiment, a combination of cultured organisms designed to benefit the health of the innate immune system may include one or more of the following probiotic organisms: *Bacteroides uniformis, Bacillus pumilus, Eubacterium rectale, Faecalibacterium prausnitzii, Lactobacillus paracasei, Lactobacillus plantarum, Lactobacillus salivarus, Streptococcus thermophilus*, and *Lactobacillus helveticus*. These probiotic organisms may be provided in an approximate CFU range of 1.00E+06-1.00E+11.

The prebiotics in Table 8 may be used in vivo to support the probiotic organisms listed as benefitting the adaptive and innate immune systems.

TABLE 8

| Prebiotic | mg/dose |
| --- | --- |
| Galacto-oligosaccharides | 500-5000 |
| Mannan-oligosaccharide | 500-5000 |
| Resveratrol | 100-1000 |
| Hesperetin | 100-1000 |
| Arabinoxylan-oligosaccharides | 500-5000 |
| Dragon fruit | 500-5000 |
| Beechwood extract xylan | 500-5000 |
| Arabinogalactan (*Larix laricina*) | 500-5000 |
| DAO antihistamine | 500-5000 |
| Xanthan gum | 500-5000 |
| Resistant starch | 500-5000 |
| Baobab fruit | 100-500 |
| Kongorobi berry | 500-5000 |
| Resveratrol/Pterostillbene | 100-500 |
| Curcumin | 100-500 |
| Indian Tinospora (*Tinospora cordifolia*) (stem and root) | 100-500 |

The amounts in Table 8 may be considered approximations. The prebiotic formulation represented in Table 8 may be hereinafter referred to as "Prebiotic Formula Theta."

Certain probiotic organisms may be used to promote or enhance physiological health more particularly for females, including without limitation, vaginal mucosal maintenance, fertility, and hormonal regulation. In one embodiment, a combination of cultured organisms designed to benefit females may include one or more of the following probiotic organisms: *Lactobacillus salivarius, Bifidobacterium longum, Bifidobacterium breve, Lactobacillus vaginalis, Lactobacillus fermentum, Lactobacillus gasseri, Lactobacillus reuteri, Lactobacillus crispatus, Lactobacillus delbrueckii* subsp. *bulgaricus, Bacteroides uniformis, Lactobacillus rhamnosus, Lactobacillus acidophilus, Lactobacillus plantarum, Lactobacillus jensenii, Bifidobacterium catenulatum*, and *Bifidobacterium pseudocatenulatum*. These probiotic organisms may be provided in an approximate CFU range of 1.00E+06-1.00E+11.

Certain probiotic organisms may be used to promote or enhance physiological health more particularly for males, including without limitation, urogenital tissue maintenance, fertility, and prostate health. In one embodiment, a combination of cultured organisms designed to benefit males may include one or more of the following probiotic organisms: *Eubacterium limosum, Lactobacillus paracasei, Bacteroides* thetaiotamicron, *Lactobacillus johnsonii, Lactobacillus acidophilus, Bifidobacterium longum, Lactobacillus curvatus, Lactobacillus brevis, Lactobacillus salivarius, Lactobacillus helveticus, Lactobacillus casei, Lactobacillus paracasei, Lactobacillus rhamnosus,* and *Clostridium scindens*. These probiotic organisms may be provided in an approximate CFU range of 1.00E+06-1.00E+11.

The prebiotics in Table 9 may be used in vivo to support at least the following probiotic organisms: *Lactobacillus vaginalis, Eubacterium limosum, Bacteroides thetaiotamicron,* and *Bacteroides uniformis*.

TABLE 9

| Prebiotic | mg/dose |
| --- | --- |
| Xylo-oligosaccharides | 500-5000 |
| Glucomannan (Amorphophallus konjac) | 500-5000 |
| Prebiosure WG extract | 500-5000 |
| Galactomannan | 500-5000 |
| Billberry (Vaccinium myrtillus) powder | 100-1000 |
| Brown seaweed (Alginate fucoidan) | 100-1000 |
| Mulberry (Morus nigra) | 100-1000 |
| Myo-inositol | 500-5000 |
| Modified citrus pectin | 100-1000 |
| Cassava root powder (Manihot esculenta) | 100-1000 |
| Glucosamino glycan | 500-5000 |
| PH guar gum (Cyamopsis tetragonolobus) Galactomannan | 500-5000 |
| Oat oligosaccharide | 500-5000 |
| Clitoria ternatea blue pea flower | 50-500 |
| Cranberry | 50-500 |
| Bearberry (*Arctostaphylos uva ursi*) | 50-500 |

The amounts in Table 9 may be considered approximations. The prebiotic formulation represented in Table 9 may be hereinafter referred to as "Prebiotic Formula Iota."

Generally, the microbiome is formed and maintained by an individual's dietary intake. Every compound, macronutrient, and micronutrient is processed by the microbiome prior to entering the blood stream. Consequently, the microbiome controls caloric response, nutrient response, and overall metabolic behavior. Although metabolism is complex, a number of organisms are involved in maintaining a healthy metabolism and the absence of these organisms in the gastrointestinal tract leads to markers of unhealthy metabolism and potential weight problems.

In one embodiment, a combination of cultured organisms designed to benefit metabolic processes may include one or more of the following probiotic organisms: *Bacillus clausii, Lactobacillus casei, Akkermansia muciniphila, Eubacterium rectale, Lactococcus lactis, Lactobacillus bulgaricus, Lactobacillus buchneri, Pediococcus acidilactici, Bifidobacterium longum, Lactobacillus brevis, Lactobacillus delbrueckii* subsp. *bulgaricus, Propionibacterium shermanii, Butyricicoccus pullicaecorum, Lactobacillus acidophilus, Lactobacillus rhamnosus* GG, *Lactobacillus gasseri, Anaerobutyricum hallii, Bifidobacterium catenulatum,* and *Bifidobacterium pseudocatenulatum*. These probiotic organisms may be provided in an approximate CFU range of 1.00E+06-1.00E+11.

The prebiotics in Table 10 may be used in vivo to support at least the following probiotic organisms: *Eubacterium rectale, Akkermansia muciniphila, Eubacterium hallii, Parabacteroides distasonis, Intestinibacter bartettii,* and *Christensenella minuta*.

TABLE 10

| Prebiotic | mg/dose |
| --- | --- |
| Bael fiber | 500-5000 |
| Fenugreek fiber | 500-5000 |
| Organic quinoa sprout | 500-5000 |
| Organic chia seed | 500-5000 |
| Organic millet sprout | 500-5000 |
| Organic buckwheat sprout | 500-5000 |
| N-acetyl glucosamine amino glycan | 500-5000 |
| Chondroitin | 50-500 |
| Mucin | 500-5000 |
| Chitosan oligo | 500-5000 |
| Carrot fiber | 500-5000 |
| Promitor (corn fiber)/Nutiose Roquett | 500-5000 |
| Acemannon | 500-5000 |
| Pea fiber | 500-5000 |
| Cutch tree (Acacia catechu)(heartwood and bark) (powder and extract) | 50-1000 |
| Pullulan | 50-1000 |
| Marshmallow root (Althaea officinalis) | 50-1000 |
| Camels milk | 500-5000 |

The amounts in Table 10 may be considered approximations. The prebiotic formulation represented in Table 10 may be hereinafter referred to as "Prebiotic Formula Kappa."

Certain probiotic organisms may be used to promote or enhance metabolic processes, including without limitation, glucose regulation, ketone regulation, and energy production. In one embodiment, a combination of cultured organisms designed to benefit metabolic processes may include one or more of the following probiotic organisms: *Bacillus clausii, Lactobacillus casei, Akkermansia muciniphila, Eubacterium rectale, Faecalibacterium prausnitzii, Bifidobacterium lactis, Lactobacillus lactis, Lactobacillus plantarum, Lactobacillus buchneri, Bacteroides thetaiotamicron, Bifidobacterium longum,* and *Lactobacillus brevis*. These probiotic organisms may be provided in an approximate CFU range of 1.00E+06-1.00E+11.

The prebiotics in Table 11 may be used in vivo to support the probiotic organisms listed as benefitting metabolic processes.

TABLE 11

| Prebiotic | mg/dose |
| --- | --- |
| Bael fiber | 500-5000 |
| Fenugreek fiber | 500-5000 |
| Organic quinoa sprout | 500-5000 |
| Organic chia seed | 500-5000 |
| Organic millet sprout | 500-5000 |
| Organic buckwheat sprout | 500-5000 |
| N-acetyl glucosamine amino glycan | 500-5000 |
| Chondroitin | 50-500 |
| Mucin | 500-5000 |
| Chitosan oligo | 500-5000 |
| Carrot fiber | 500-5000 |
| Promitor (corn fiber)/Nutiose Roquett | 500-5000 |
| Acemannon | 500-5000 |
| Pea fiber | 500-5000 |
| Cutch tree (Acacia catechu)(heartwood and bark) (powder and extract) | 50-1000 |
| Pullulan | 50-1000 |

The amounts in Table 11 may be considered approximations. The prebiotic formulation represented in Table 11 may be hereinafter referred to as "Prebiotic Formula Lambda."

The mouth, esophagus and stomach have a unique microbiome that is not normally supported by typical probiotics and prebiotics. Certain cultivation and delivery modes are required to support the microbiota found in the mouth, esophagus and stomach tissues. The design of a combination of probiotics for the mouth, esophagus and stomach utilizes research on the upper gastrointestinal microbiota, specific species, growth conditions and requirements followed by differential stabilization in a powder dosage form.

In one embodiment, a combination of cultured organisms designed to benefit the mouth, esophagus and stomach may include one or more of the following probiotic organisms: *Streptococcus uberis, Streptococcus oralis, Streptococcus rattus, Streptococcus salivarius, Saccharomyces cerevisiae, Bacillus coagulans, Mycobacterium vaccae, Lactobacillus salivarius, Lactobacillus helveticus, Lactobacillus fermentum, Bifidobacterium lactis, Enterococcus faecalis, Lactobacillus kefiri,* and *Butyricicoccus pullicaecorum.* These probiotic organisms may be provided in an approximate CFU range of 1.00E+06-1.00E+11.

In one embodiment, a combination of cultured organisms designed to benefit the mouth, esophagus and stomach may include one or more of the following probiotic organisms: *Bifidobacterium lactis, Lactobacillus brevis, Lactobacillus paracasei, Lactobacillus reuteri, Lactobacillus salivarius, Streptococcus salivarius, Lactobacillus casei, Lactobacillus acidophilus, Lactobacillus plantarum, Streptococcus uberis* (KJ2®), *Streptococcus oralis* (KJ3®), and *Streptococcus rattus* (JH145®). These probiotic organisms may be provided in an approximate CFU range of 1.00E+06-1.00E+11.

In one embodiment, a combination of cultured organisms designed to benefit the endocrine system, autocrine, may include one or more of the following probiotic organisms: *Bacteroides uniformis, Eubacterium limosum, Bacillus indicus, Lactobacillus iners, Bacillus megaterium, Lactobacillus johnsonii, Lactobacillus delbrueckii* subsp. *bulgaricus, Lactobacillus acidophilus, Bacillus coagulans,* and *Bacteroides thetaiotamicron.* These probiotic organisms may be provided in an approximate CFU range of 1.00E+06-1.00E+11.

In one embodiment, a combination of cultured organisms designed to benefit the endocrine system, paracrine, may include one or more of the following probiotic organisms: *Bacillus coagulans, Bifidobacterium longum, Bifidobacterium breve, Eubacterium limosum, Lactobacillus fermentum, Lactobacillus gasseri, Lactobacillus reuteri, Lactobacillus vaginalis, Lactobacillus rhamnosus A, Lactobacillus crispatus, Lactobacillus iners,* and *Lactobacillus delbrueckii* subsp. *bulgaricus.* These probiotic organisms may be provided in an approximate CFU range of 1.00E+06-1.00E+11.

The prebiotics in Table 12 may be used in vivo to support the probiotic organisms listed as benefitting the endocrine system.

TABLE 12

| Prebiotic | mg/dose |
|---|---|
| Glycomacropeptide | 500-5000 |
| Xylo-oligosaccharides | 500-5000 |
| Glucomannan (Amorphophallus konjac) | 500-5000 |
| Prebiosure WG extract | 500-5000 |
| Galactomannan | 500-5000 |
| Blueberry | 100-1000 |
| Thymus | 100-1000 |
| Mulberry (Morus nigra) | 100-1000 |
| Myo-inositol | 500-5000 |
| Modified citrus pectin | 100-1000 |
| Tapioca | 100-1000 |
| Glucosamino glycan | 500-5000 |
| PH guar gum (Cyamopsis tetragonolobus) Galactomannan | 500-5000 |
| Oat oligosaccharide | 500-5000 |
| Clitoria ternatea blue pea flower | 50-500 |

TABLE 12-continued

| Prebiotic | mg/dose |
|---|---|
| Cranberry | 50-500 |
| Bearberry (*Arctostaphylos uva ursi*) | 50-500 |

The amounts in Table 12 may be considered approximations. The prebiotic formulation represented in Table 12 may be hereinafter referred to as "Prebiotic Formula Mu."

Certain probiotics may be more beneficial for children because there are so many developmental processes that rely on a healthy microbiome, and they need a constant supply of healthy prebiotic oligosaccharides.

In one embodiment, a combination of cultured organisms designed to benefit children may include one or more of the following probiotic organisms: *Bifidobacterium animalus, Bifidobacterium infantis, Bifidobacterium adolescentis, Lactobacillus gasseri, Lactococcus lactis, Bifidobacterium longum pseudo, Lactobacillus bulgaricus,* and *Bacteroides ovatus.* These probiotic organisms may be provided in an approximate CFU range of 1.00E+06-1.00E+11.

The prebiotics in Table 13 may be used in vivo to support the probiotic organisms listed as benefitting children.

TABLE 13

| Prebiotic | mg/dose |
|---|---|
| 2'frucosyllactose | 500-5000 |
| Isomalto-oligosaccharide | 500-5000 |
| Fructo-oligosaccharide | 500-5000 |
| Galacto-oligosaccharide | 500-5000 |
| Rutin | 100-1000 |
| Oat oligolactolipids | 500-5000 |
| Sialylated bovine milk oligosaccharides (S-BMO) | 100-5000 |
| IgY-immunoglobulin (IgY MAX ®) | 25-500 |
| Beta glucan | 100-1000 |
| Maca | 100-1000 |
| Lacto-oligosaccharide | 100-1000 |
| Medium chain triglycerides | 500-5000 |
| Phosphatidyl choline | 500-5000 |
| Rose hips | 500-5000 |

The amounts in Table 13 may be considered approximations. The prebiotic formulation represented in Table 13 may be hereinafter referred to as "Prebiotic Formula Nu."

Fermented probiotics can provide substantial health benefits, but ferments often contain contaminants and can affect the gastrointestinal tract in negative ways. Providing a substantially pure combination of probiotics in a stable, powder form can provide all the benefits of fermented organisms and their metabolites, with the complications that come from contaminants. For example and not by way of limitation, a stable, powder product may include freeze-dried kefir, freeze-dried kombucha sobas, DAO (diamineoxidase) porcine, and kidney protein concentrate.

In one embodiment, a combination of cultured organisms that may be included in a stable, powder product and designed to provide the benefits of fermented organisms and their metabolites may include one or more of the following probiotic organisms: *Bacillus pumilus, Desulfovibrio piger, Lactococcus lactis, Lactobacillus sakei, Propionibacterium freundenreichii, Lactobacillus helveticus,* and *Saccharomyces cerevisiae.* These probiotic organisms may be provided in an approximate CFU range of 1.00E+06-1.00E+11.

The subject invention may be more easily comprehended by reference to the specific embodiments recited herein, which are representative of the invention. However, it must be understood that the specific embodiments are provided

What is claimed and desired to be secured by United States Letters Patent is:

1. A method for producing a probiotic product designed to promote and maintain immune system function comprising:
   selecting at least one probiotic organism from the group consisting of *Collinsella aerofaciens, Anaerostipes caccae, Bacteroides ovatus, Clostridium symbiosum,* and *Roseburia nominis;*
   selecting a growth broth for growing the probiotic organism, wherein the growth broth comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of diamine oxidase (DAO) antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin;
   inoculating the growth broth with the probiotic organism;
   growing the probiotic organism in the growth broth;
   harvesting the probiotic organism from the growth broth;
   selecting an agar spread plate for growing the probiotic organism, wherein the agar spread plate comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of DAO antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin;
   inoculating the agar spread plate with the probiotic organism harvested from the growth broth;
   growing the probiotic organism on the agar spread plate;
   harvesting the probiotic organism from the agar spread plate; and
   freeze-drying the probiotic organism.

2. The method of claim 1, further comprising:
   freeze-drying the probiotic organism harvested from the agar spread plate by use of a lyophilization reagent, wherein the lyophilization reagent comprises mannitol, trehalose, glycerol, cysteine, ascorbic acid, glutathione, uric acid, and activated charcoal.

3. The method of claim 1, wherein the agar spread plate media further comprises approximately 40 g/L tryptic soy agar, approximately 50 ml/L defibrinated sheep blood, approximately 0.5 g/L cysteine, and approximately 0.1 g/L glutathione.

4. The method of claim 1, wherein the at least one probiotic organism is selected from the group consisting of *Bacteroides ovatus* and *Anaerostipes caccae.*

5. A method for growing a probiotic organism comprising:
   selecting at least one probiotic organism from the group consisting of *Collinsella aerofaciens, Anaerostipes caccae, Bacteroides ovatus, Clostridium symbiosum, Roseburia nominis, Bacteroides uniformis, Bacteroides fragilis, Pediococcus acidilactici, Butyricicoccus pullicaecorum,* and *Dorea longicatena;*
   selecting a growth broth for growing the probiotic organism, wherein the growth broth comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of diamine oxidase (DAO) antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin;
   inoculating the growth broth with the probiotic organism;
   growing the probiotic organism in the growth broth;
   harvesting the probiotic organism from the growth broth;
   selecting an agar spread plate media for growing the probiotic organism, wherein the agar spread plate media comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of DAO antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin;
   inoculating the agar spread plate media with the probiotic organism harvested from the growth broth;
   growing the probiotic organism on the agar spread plate; and
   harvesting the probiotic organism from the agar spread plate.

6. The method of claim 5, further comprising: freeze-drying the probiotic organism.

7. The method of claim 6, further comprising: including the probiotic organism after freeze-drying with a product preservative, wherein the product preservative comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of DAO antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin.

8. The method of claim 6, wherein the freeze-drying includes use of a freeze-drying buffer that comprises 10% mannitol, 12.5% sucrose, 2.5% trehalose, 1.0% glycerol, 10% skim milk, 0.2% cysteine, 0.1% ascorbic acid, 0.05% glutathione, 0.05% uric acid, and 2.0% charcoal in deionized water and adjusted to pH 7 with potassium hydroxide.

9. The method of claim 5, further comprising: freeze-drying the probiotic organism harvested from the agar spread plate by use of a lyophilization reagent, wherein the lyophilization reagent includes at least two compounds selected from the group consisting of glucosamine, glutamine, sucrose, mannitol, trehalose, glycerol, inositol, raffinose, inulin, powdered skim milk, activated charcoal, soluble starch, collagen powder, chondroitin sulfate, glucosamine sulfate, guar, acacia, silica, and fructooligosaccharide P95.

10. The method of claim 5, further comprising: including the probiotic organism in a nutritional supplement product.

11. The method of claim 9, further comprising: including the probiotic organism in a nutritional supplement product.

12. A method for growing a probiotic organism comprising:
   selecting at least two probiotic organisms from the group consisting of *Collinsella aerofaciens, Anaerostipes caccae, Bacteroides ovatus, Clostridium symbiosum, Roseburia nominis, Bacteroides uniformis, Bacteroides fragilis, Pediococcus acidilactici, Butyricicoccus pullicaecorum*, and *Dorea longicatena*;
   selecting a growth broth for growing the probiotic organisms, wherein the growth broth comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of diamine oxidase (DAO) antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin;
   inoculating the growth broth with the probiotic organisms;
   growing the probiotic organisms in the growth broth;
   harvesting the probiotic organisms from the growth broth;
   selecting an agar spread plate media for growing the probiotic organisms, wherein the agar spread plate media comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of DAO antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin;
   inoculating the agar spread plate media with the probiotic organisms harvested from the growth broth;
   growing the probiotic organisms on the agar spread plate; and
   harvesting the probiotic organisms from the agar spread plate.

13. The method of claim 12, further comprising: freeze-drying the probiotic organisms.

14. The method of claim 12, further comprising: freeze-drying the probiotic organisms harvested from the agar spread plate by use of a lyophilization reagent, wherein the lyophilization reagent includes at least two compounds selected from the group consisting of glucosamine, glutamine, sucrose, mannitol, trehalose, glycerol, inositol, raffinose, inulin, powdered skim milk, activated charcoal, soluble starch, collagen powder, chondroitin sulfate, glucosamine sulfate, guar, acacia, silica, and fructooligosaccharide P95.

15. The method of claim 13, further comprising: including the probiotic organisms after freeze-drying with a product preservative, wherein the product preservative comprises 500-5000 mg of Bimuno™-galacto-oligosaccharides, 500-5000 mg of Mannan-oligosaccharide, 100-1000 mg of Resveratrol, 100-1000 mg of Hesperetin, 500-5000 mg of Arabinoxylan-oligosaccharides, 500-5000 mg of Dragon fruit, 500-5000 mg of Beechwood extracted xylan, 500-5000 mg of Arabinogalactan, 500-5000 mg of DAO antihistamine, 500-5000 mg of Xanthan gum, 500-5000 mg of Resistant starch, 100-500 mg of Baobab fruit, 500-5000 mg of Kongorobi berry, 100-500 mg of a combination of Resveratol and Pterostillbene, 100-500 mg of Curcumin, 100-500 mg of stem and root of Indian Tinospora, 100-500 mg of Poria mushroom, and 500-5000 mg of Nobiletin.

16. The method of claim 12, further comprising: including the probiotic organisms in a nutritional supplement product.

17. The method of claim 12, further comprising: including the probiotic organisms in a topical application product.

18. The method of claim 15, further comprising: including the probiotic organisms in a nutritional supplement.

19. The method of claim 13, wherein the freeze-drying includes use of a freeze-drying buffer that comprises 10% mannitol, 12.5% sucrose, 2.5% trehalose, 1.0% glycerol, 10% skim milk, 0.2% cysteine, 0.1% ascorbic acid, 0.05% glutathione, 0.05% uric acid, and 2.0% charcoal in deionized water and adjusted to pH 7 with potassium hydroxide.

* * * * *